United States Patent [19]

Girard

[11] 4,327,450

[45] May 4, 1982

[54] METHOD OF INTRAOCULAR IMPLANTING AN ARTIFICIAL LENS

[76] Inventor: Louis J. Girard, Twelve Oaks Tower, Ste. 500, 4126 Southwest Freeway, Houston, Tex. 77027

[21] Appl. No.: 232,656

[22] Filed: Feb. 9, 1981

[51] Int. Cl.³ ............................ A61F 1/16; A61F 1/24
[52] U.S. Cl. .......................................... 3/13; 128/1 R; 128/334 R
[58] Field of Search ............. 3/13, 1; 128/1 R, 334 R, 128/305

[56] References Cited

U.S. PATENT DOCUMENTS 4,041,552  8/1977  Ganias ........................................ 3/13
4,257,130  3/1981  Bayers ........................................ 3/13

FOREIGN PATENT DOCUMENTS 810232  3/1959  United Kingdom ..................... 3/13

OTHER PUBLICATIONS

"The Weightless Intraocular Lens" by R. C. Troutman, Ophthalmic Surgery, vol. 8, No. 3, Jun. 1977, pp. 153-155.

Primary Examiner—Ronald L. Frinks

[57] ABSTRACT

A surgical method of making an intraocular implant of an artificial lens having attaching loops on opposed sides thereof. The invention contemplates incising the sclera of the eye rearwardly of the iris at opposed positions and excising the vitreous base adjacent to the incisions. Thereafter the implant is drawn through one of the incisions and sutured in position by attachment to the sclera and at a position rearwardly of the iris.

3 Claims, 4 Drawing Figures 4,327,450

METHOD OF INTRAOCULAR IMPLANTING AN ARTIFICIAL LENS

BACKGROUND OF THE INVENTION

A. Field of the Invention

This invention relates to a surgical method of intraocular implanting an artificial lens within the eye.

B. Background of the Invention

The various types of phacoprosthesis presently available all have some types of problems. The anterior chamber implants can cause endothelial damage, particularly if they are not well fixated. Iris fixated implants can erode through the iris, prevent pupil dilation, cause endothelial damage and subluxate or dislocate. Posterior chamber lenses can decenter, tilt or dislocate. All present implants can cause damage to the endothelium during insertion through the anterior chamber.

B. SUMMARY OF THE INVENTION

It is therefore an object of the present invention to provide an improved method for making such implant. The pars plana phacoprosthesis of this invention contemplates an implant designed to be inserted through the pars plana and fixated to the sclera in that area. It can be inserted primarily or secondarily.

Briefly stated, the invention is a surgical method of intraocular implanting an artificial lens having connecting means such as loops attached to opposed sides thereof. The invention contemplates incising the sclera of the eye rearwardly of the iris at opposed positions such as twelve o'clock and six o'clock with one of the incisions being enlarged and of sufficient length to accommodate passage of the lens therethrough. After excising the sclera, the vitreous base adjacent thereto is also excised, leaving a space for receipt of the artificial lens. Thereafter, the lens is inserted through the enlarged incision by drawing therethrough with a suture or the like. Thereafter, the lens is connected in place by attaching the loops of the lens to the sclera of the eye to thereby fix the lens in position rearwardly of the iris and firmly attached to the sclera.

DESCRIPTION OF THE PREFERRED EMBODIMENT

Figure 1:
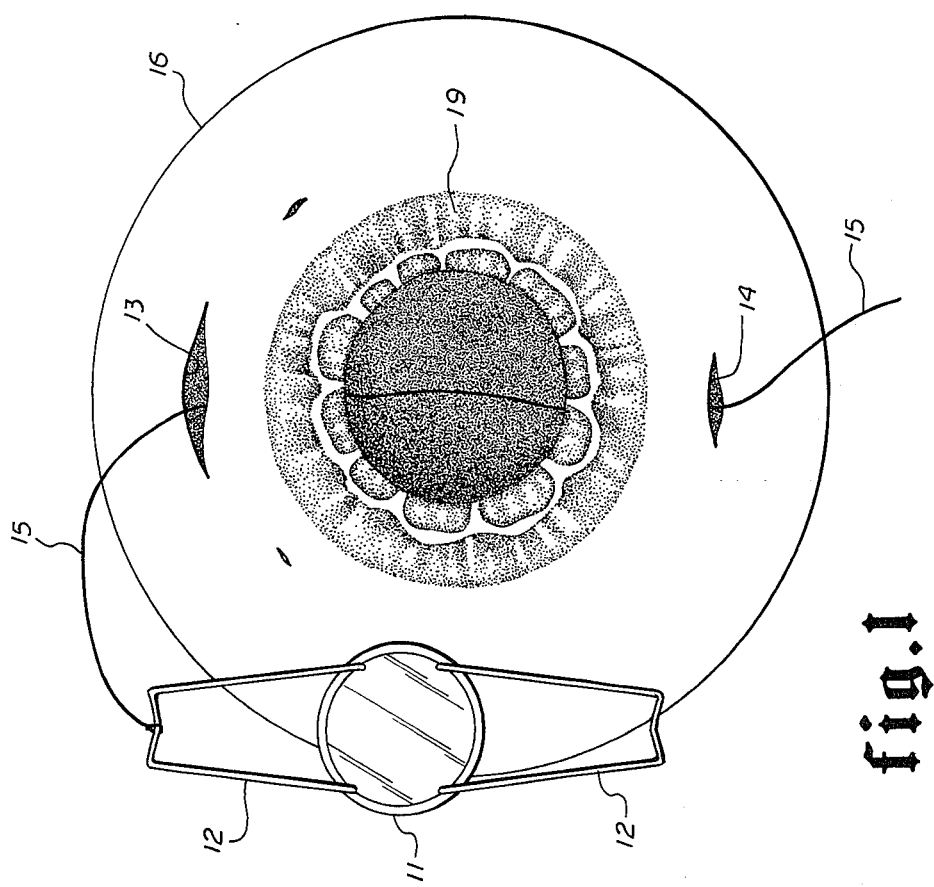
FIG. 1 is a front elevation view, partially schematic, showing the forward surface of an eye globe having the incisions made and just prior to inserting the artificial lens thereinto.

Referring now to FIG. 1, the implant consists of a round optic lens 11 of polymethylmethacrylate which is 5 mm. in diameter with two polypropylene loops attached to and extending in opposite directions. The ends of loops 12 are formed in an "M" configuration. The distance between the tips of loops 12 is preferably about 16.5 mm.

The optic lens is one manufactured by IOLAB corporation of 560 West Terrace Way, San Dimas, Calif. 91773.

The implant may be inserted after pars plana lensectomy by ultrasonic fragmentation or in an aphakic eye. The sclera of the eye globe is exposed at 12 and 6 o'clock. A caliper is used to check the length of the implant and the caliper checked against a millimeter ruler. The caliper is then placed against the sclera equidistant from the limbus at 12 and 6 o'clock and these points marked with a cautery. If the caliper is set at 16.5 mm., the marks are usually 3 mm. from the limbus.

The caliper is then set at 5 mm. and the sclera marked on either side of the 12 o'clock mark. The sclera is incised between the marks and the pars plana exposed and gently cauterized as shown by incisions 13 and 14 in FIG. 1. The cataract is removed by pars plana lensectomy by USF. Incision 14 is a 2 mm. stab incision, made with a knife through sclera and pars plana at 6 o'clock. Incision 13 is through the pars plana at 12 o'clock and is opened with a knife and the incision extended with scissors. The vitreous base in the two incisions is excised by the ultrasonic fragmentation or the like.

Figure 2:
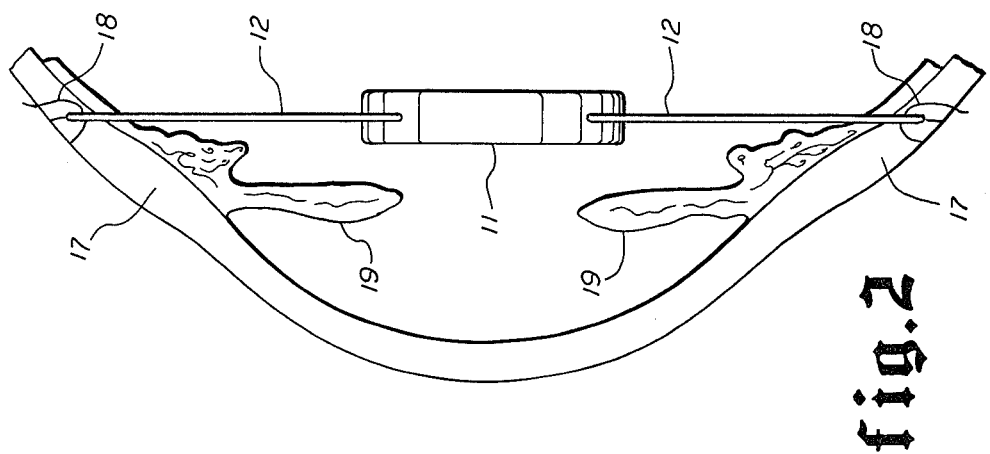
FIG. 2 is a schematic central sectional view generally through the forward portion of the eye globe and showing artificial lens in the implanted position.
Figure 4:
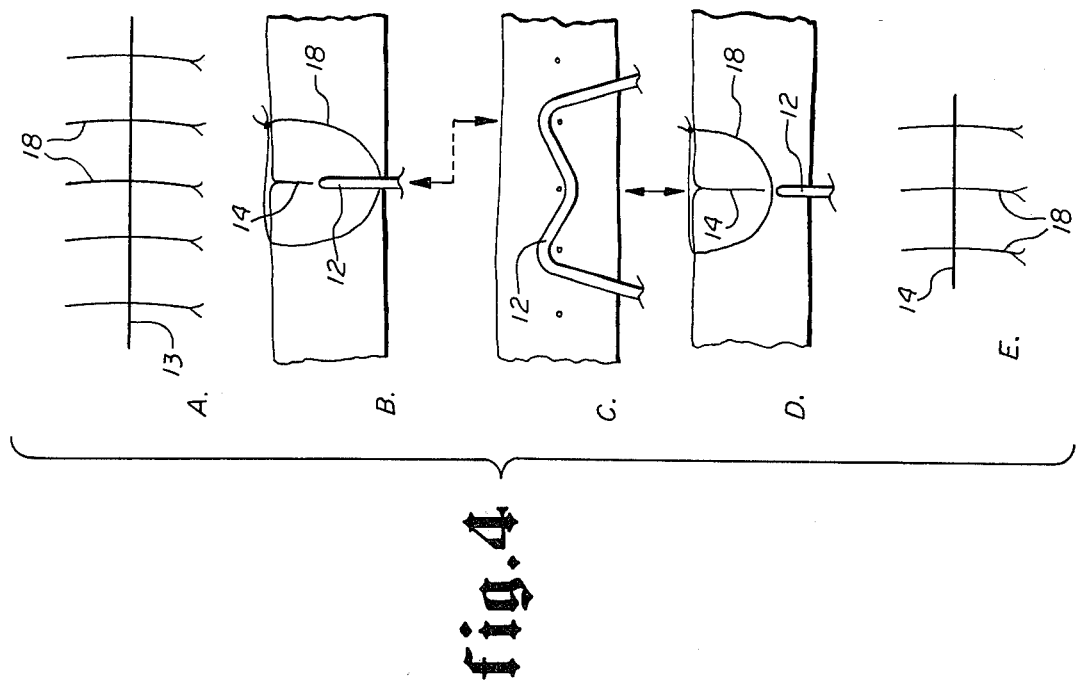
FIG. 4 are various views showing the steps and arrangement of the sutures for catching the lens to the sclera.
Figure 3:
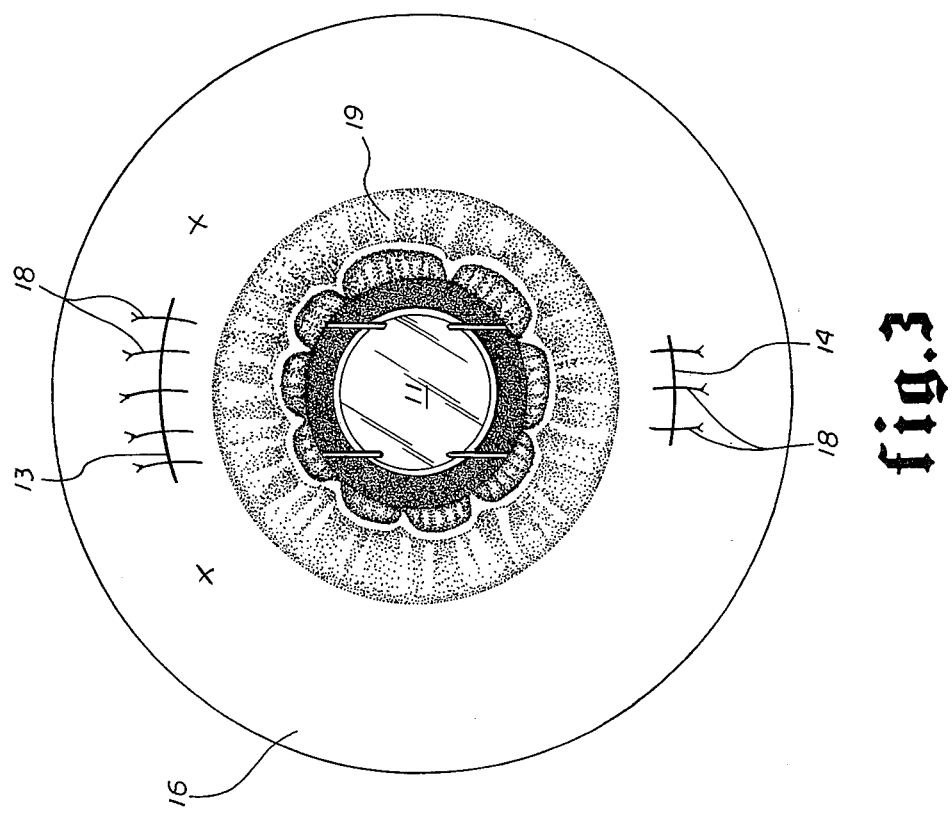
FIG. 3 is a generally schematic front elevation view showing the implanted lens in position and the incisions sutured shut.

Using a large curved needle (not shown), a 9-0 Prolene suture 15 is passed from the 6 o'clock incision 14 out the 12 o'clock incision 13. Suture 15 is tied to one of the loops 12 of implant lens 11. The implant lens is then inserted through 12 o'clock incision 13 and drawn into the globe 16 of the eye by suture 15. When loops 12 are in position, they are sutured to sclera 17 with three interrupted 9-0 Prolene sutures 18 as shown in FIGS. 2-4. Two of the sutures pass through deep sclera and inside loops 12. A single suture is passed through superficial sclera and anterior to the notch of loops 12. In this manner, loops 12 are imbricated into the scleral incisions 13 and 14 and are prevented from extruding or intruding. Lens 11 is thus positioned just rearwardly of iris 19.

The irrigator and fragmentor needles are reinserted into globe 16 and any blood from the implantation lavaged and globe 16 reformed.

The remainder of the sclerotomy incisions are closed with interrupted 6-0 polyglactin sutures. The conjunctival and tenon's incisions are closed with a running 6-0 plain cutgut suture as shown in FIGS. 3 and 4. An antibiotic and steroid are injected subconjunctivally.

There are several advantages to pars plana phacoprosthesis. The implant is firmly anchored to the sclera, the most durable part of the eye. The posterior chamber position of the optic assures the best optical result. The pupil can be dilated for fundus examination. Implantation causes no damage to the corneal endothelium or iris. Bleeding has not been a problem. No retinal dialyses have occurred. Fibrovascular ingrowth has not proven to be a problem. Cystoid macular edema can occur but apparently not more frequently than with pars plana lensectomy or intracapsular extraction alone.

There are other advantages of the pars plana phacoprosthesis. It can be used in eyes with traumatized irises or aniridia. It can be used for any size globe (the length of the loops can be specially ordered). There is no danger of loss of the anterior chamber.

There is thus provided a new intraocular implant method where the lens implant is inserted through the pars plana and is anchored to the sclera in that area. The optic is positioned in the posterior chamber allowing free movement of the iris and best optical correction.

Further modifications and alternative embodiments of the apparatus of this invention will be apparent to those skilled in the art in view of this description. Accordingly, this description is to be construed as illustrative only and is for the purpose of teaching those skilled in the art the manner of carrying out the invention. It is to be understood that the form of the invention herewith shown and described is to be taken as the presently preferred embodiment. Various changes may be made in the shape, size and arrangement of parts. For example, equivalent elements or materials may be substituted for those illustrated and described herein, parts may be reversed, and certain features of the invention may be utilized independently of the use of other features, all as would be apparent to one skilled in the art after having the benefit of this description of the invention.

What is claimed is:

1. In a surgical method of intraocular implanting an artificial lens having connecting means attached to opposed sides thereof, the steps comprising:

incising the sclera of the eye which is being implanted rearwardly of the iris at opposed positions, with one of said incisions being enlarged and of sufficient length to accommodate passage of said lens therethrough;

excising the vitreous base adjacent said two incisions;

inserting the lens through said enlarged incision;

and attaching the connecting means of said lens to the sclera of the eye at opposed positions to fix said lens in said eye.

2. The invention as claimed in claim 1 wherein:

said connecting means includes a pair of flexible loops, and said lens is inserted into said eye by attaching suture means to one of said loops and drawing said lens and loops into said eye by pulling on said suture means.

3. The invention as claimed in claim 2 wherein:

said loops of said lens are attached to the sclera by suturing the same in place proximate said incisions.

* * * * *